United States Patent
Park et al.

(10) Patent No.: US 9,028,563 B2
(45) Date of Patent: May 12, 2015

(54) FOAM-TYPE HAIR DYE COMPOSITION FOR IMPROVING HAIR SOFTNESS WITHOUT DRIPPING

(71) Applicant: Amorepacific Corporation, Seoul (KR)

(72) Inventors: Jae Jung Park, Yongin-si (KR); Hyo Seung Moon, Yongin-si (KR); Jong Hyub Kim, Yongin-si (KR); Wang Gi Kim, Yongin-si (KR); Sang Hoon Kim, Yongin-si (KR); Jang Won Choi, Yongin-si (KR)

(73) Assignee: Amorepacific Corporation, Seoul (KR)

( * ) Notice: Subject to any disclaimer, the term of this patent is extended or adjusted under 35 U.S.C. 154(b) by 0 days.

(21) Appl. No.: 14/359,981

(22) PCT Filed: Nov. 16, 2012

(86) PCT No.: PCT/KR2012/009724
§ 371 (c)(1),
(2) Date: May 22, 2014

(87) PCT Pub. No.: WO2013/077599
PCT Pub. Date: May 30, 2013

(65) Prior Publication Data
US 2014/0345065 A1    Nov. 27, 2014

(30) Foreign Application Priority Data
Nov. 24, 2011  (KR) ........................ 10-2011-0123389

(51) Int. Cl.
*A61Q 5/10*  (2006.01)
*A61K 8/04*  (2006.01)
(Continued)

(52) U.S. Cl.
CPC ......... *A61K 8/046* (2013.01); *A61K 2800/4322* (2013.01); *A61K 8/39* (2013.01);
(Continued)

(58) Field of Classification Search
CPC ........... A61Q 5/10; A61K 8/046; A61K 8/22; A61K 8/39; A61K 2201/326; A61K 2201/928; A61K 2800/4322; A61K 2800/5426
USPC .............................. 8/405, 406, 554, 582, 477
See application file for complete search history.

(56) References Cited

U.S. PATENT DOCUMENTS

| | | | |
|---|---|---|---|
| 6,572,663 | B1 | 6/2003 | Pitfield et al. |
| 7,423,776 | B2 | 9/2008 | Murata |

(Continued)

FOREIGN PATENT DOCUMENTS

| | | |
|---|---|---|
| JP | 2002-508305 A | 3/2002 |
| JP | 2002-511064 A | 4/2002 |

(Continued)

OTHER PUBLICATIONS

International Searching Authority, International Search Report for PCT/KR2012/009724 dated Mar. 22, 2013.

*Primary Examiner* — Eisa Elhilo
(74) *Attorney, Agent, or Firm* — Sughrue Mion, PLLC

(57) ABSTRACT

The present invention relates to a hair dye composition, and more particularly, to a foam-type hair dye composition comprising: a first agent including a dye and an alkaline agent and a second agent including an oxidant; and a nonionic viscosity increasing agent of a PEG-aliphatic acid ester or a PPG-aliphatic acid ester in one or both of the first agent and the second agent, thereby largely improving dyeing properties without dripping after the composition is coated on hair.

11 Claims, 1 Drawing Sheet

(51) Int. Cl.
*A61K 8/39* (2006.01)
*A61Q 5/02* (2006.01)
*A61K 8/86* (2006.01)

(52) U.S. Cl.
CPC . *A61Q 5/02* (2013.01); *A61Q 5/10* (2013.01); *A61K 8/86* (2013.01); *A61K 2800/48* (2013.01); *A61K 2800/882* (2013.01)

(56) References Cited

U.S. PATENT DOCUMENTS

| 7,887,600 | B2 | 2/2011 | Bureiko et al. | |
|---|---|---|---|---|
| 2003/0024059 | A1* | 2/2003 | Pratt et al. | 8/405 |
| 2012/0237465 | A1* | 9/2012 | Tamareselvy et al. | 424/59 |
| 2014/0147402 | A1* | 5/2014 | Klug et al. | 424/62 |

FOREIGN PATENT DOCUMENTS

| JP | 2009-235013 A | 10/2009 |
|---|---|---|
| JP | 2009-541300 A | 11/2009 |

* cited by examiner

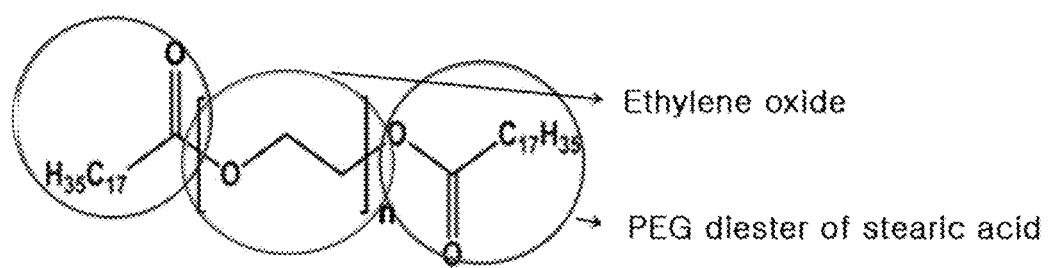

FOAM-TYPE HAIR DYE COMPOSITION FOR IMPROVING HAIR SOFTNESS WITHOUT DRIPPING

TECHNICAL FIELD

The present invention relates to a hair dye composition, and more particularly to a foam-type hair dye composition comprising: a first agent containing a dye and an alkaline agent; and a second agent containing an oxidizing agent, wherein at least one of the first agent and the second agent contains PEG-fatty acid ester or PPG-fatty acid ester that is a nonionic thickener.

BACKGROUND ART

As the standard of living has been raised and public interest in beauty has increased, the desire to express oneself through cosmetics has also increased. Hair dyeing is an immediate and reliable method for expressing the individuality of oneself and making changes. For this reason, in the modern society, hair dyeing has become popular among people of all ages and both sexes.

In a typical and general of using hair dyes, a dye-containing first agent in the form of cream or lotion is mixed with a second agent containing an oxidizing agent, and the mixture is applied to hair. However, with an increase in the demand for a convenient dyeing method capable of easily dyeing hair by oneself at home, not in a hair shop, foam dyeing is receiving increasing attention.

Foam-type hair dyes are largely divided into an aerosol-type hair dye and a non-aerosol-type hair dye. The aerosol-type hair dye is in a state in which the content is mixed with gas so that the content is discharged by the pressure of the gas. On the other hand, the non-aerosol-type hair dye contains no gas and is configured to form foam when the content passes through a foaming mesh. The aerosol-type hair dye has an advantage in that the content is conveniently used several times, but when it is used in stylish dyeing that requires a large amount of the dye at a time, its efficiency versus the price of the material can be reduced.

Foam-type hair dyes are receiving increasing attention, because they can be easily and conveniently applied to hair even by the user's hand by shampooing the hair. However, the hair dyes also have a disadvantage in that, if the time for which the hair dye is applied to and maintained on hair is long, the content of the hair dye can flow down due to its low viscosity compared to a cream-type product, and for this reason, it is difficult to uniformly dye hair with the hair dye. In addition, the foam-type hair dye has low adhesion to hair, and thus the abilities of the hair dye to dye and decolorize hair are significantly low compared to those of a cream-type product. Further, the foam-type hair dye can cause great damage to hair.

Thus, there is an urgent need for a foam-type dyeing agent, the content of which can be easily and conveniently applied to hair without flowing down and which has excellent dyeing and decolorizing abilities and show minimized damage to hair.

Meanwhile, conventional foam-type hair dyes contain either an anionic surfactant having excellent foam-forming ability or a large amount of an amphoteric surfactant and a polymeric thickener in order to increase the elasticity of foam. However, the use of the anionic surfactant can cause additional irritation or reduce the dyeing ability, and the use of a large amount of the amphoteric surfactant can significantly reduce the dyeing ability compared to the use of the anionic surfactant. In addition, the use of the polymeric thickener enables foam immediately after discharge to be elastic, but there is a problem that, if the foam is allowed to stand on hair for a long time after application, it easily collapses so that the content easily flows down.

In addition, cationic polymers having a significant effect on hair conditioning are not contained in large amounts in the first agent or the second agent in terms of the stability of the content and also show a significant difference in hair conditioning therebetween. Thus, the selection and blending of a conditioning material suitable for a foam formulation are very important.

DISCLOSURE

Technical Problem

Accordingly, the present inventors have conducted continued studies on a method capable of overcoming the limitations of conventional foam-type hair dyes and maximizing customer satisfaction in terms of usability, dyeing ability and hair damage, and as a result, have found that a two-agent type foam-type hair dye composition containing a fatty acid diester that is a nonionic thickener forms a more elastic foam that does not easily collapse, and thus has increased dyeing quality and can also ensure excellent hair conditioning properties.

Therefore, it is an object of the present invention to provide a foam-type hair dye composition that forms a more elastic and long-lasting foam, and thus has increased usability and dyeing quality.

Technical Solution

In order to accomplish the above object, the present invention provides a hair dye composition containing at least one of compounds represented by the following formulas 1 to 4:

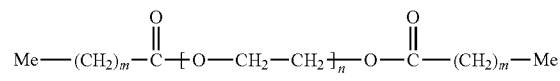

Formula 1 wherein m is an integer ranging from 11 to 21, and n is an integer ranging from 100 to 150;

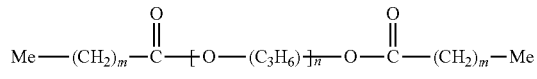

Formula 2 wherein m is an integer ranging from 11 to 21, and n is an integer ranging from 100 to 150;

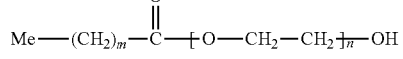

Formula 3 wherein m is an integer ranging from 11 to 21, and n is an integer ranging from 100 to 150;

Formula 4

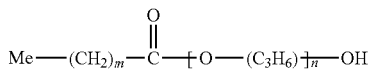

wherein m is an integer ranging from 11 to 21, and n is an integer ranging from 100 to 150.

Advantageous Effects

The foam-type hair dye composition according to the present invention can form a foam that has high adhesion to hair, and thus the content thereof does not flow down even when it is allowed to stand for a long time after application to hair. Thus, it can be easily applied to hair by the user's hand and has greatly increased dyeing quality and greatly reduced hair damage to provide excellent hair conditioning properties.

DESCRIPTION OF DRAWINGS

FIG. 1 shows polyethylene glycol distearate that is a compound of formula 1 wherein m is 16 and n is 150.

BEST MODE

The present invention is directed to a foam-type hair dye composition, and more particularly to a foam-type hair dye composition which is composed of a first agent containing a dye and an alkaline agent and a second agent containing an oxidizing agent and forms a foam that is more elastic and can last for a long period of time.

The foam-type hair dye composition of the present invention contains at least one nonionic thickener of PEG (polyethylene glycol)-fatty acid diester, PPG (polypropylene glycol)-fatty acid diester, PEG-fatty acid monoester and PPG-fatty acid monoester in at least one of the first agent and the second agent in order to form a desired foam. The above PEG-fatty acid diester, PPG-fatty acid diester, PEG-fatty acid monoester and PPG-fatty acid monoester are represented by the following formulas 1 to 4, respectively:

Formula 1

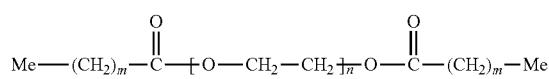

wherein m is an integer ranging from 11 to 21, and n is an integer ranging from 100 to 150;

Formula 2

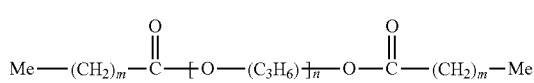

wherein m is an integer ranging from 11 to 21, and n is an integer ranging from 100 to 150;

Formula 3

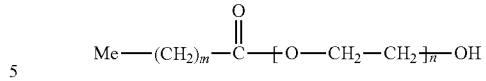

wherein m is an integer ranging from 11 to 21, and n is an integer ranging from 100 to 150;

Formula 4

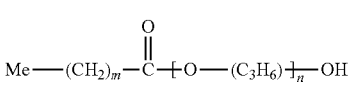

wherein m is an integer ranging from 11 to 21, and n is an integer ranging from 100 to 150.

In addition, the composition of the present invention may preferably contain at least one nonionic thickener selected from among a compound of the following formula 5 and a compound of the following formula 6, and more preferably, it may contain the compound of formula 5 that is polyethylene glycol distearate (see FIG. 1 regarding the detailed structure thereof):

Formula 5

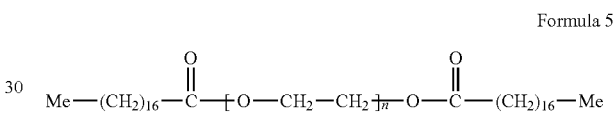

wherein n is an integer ranging from 100 to 150;

Formula 6

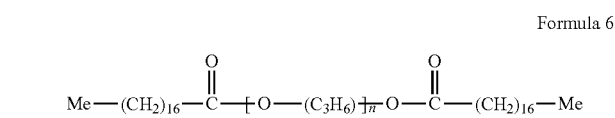

wherein n is an integer ranging from 100 to 150.

In the present invention, the nonionic thickener is contained in an amount of 0.1-5 wt %, and preferably 0.5-2 wt, based on the total weight of the composition (that is, the sum of the weights of a first agent and a second agent in the case of a two-agent type composition, and the sum of the weights of a first agent, a second agent and a third agent in the case of a three-agent type composition). If the content of the nonionic thickener in the composition is less than 0.1 wt %, the effect thereof will be insignificant, and if the content is more than 5 wt %, the viscosity of the content will be greatly increased, making it difficult to discharge the content.

Further, the composition of the present invention may contain, in addition to the nonionic thickener, a foaming agent in order to increase the foam-forming ability. The foaming agent that is additionally used may be contained in any of the first agent, the second agent and the third agent. The kind of foaming agent used is not specifically limited, but a nonionic foaming agent is preferably used in the present invention.

The first agent in the hair dye composition of the present invention may contain an oxidation dye precursor and a coupler, which are generally used in the art. Preferably, it may contain two or more oxidation dye precursors and couplers. Examples of the oxidation dye precursor that is used in the present invention include, but are not limited to, o-aminophenol, p-aminophenol, p-phenylenediamine, toluene-2,5-diamine hydrochloride, p-phenylenediamine hydrochloride, toluene-2,5-diamine, p-phenylenediamine sulfate, p-methylaminophenol sulfate, o-aminophenol sulfate, p-aminophenol sulfate, toluene-2,5-diamine sulfate, and p-phenylenediamine sulfate.

The coupler that is used in the present invention may be any coupler that is mixed with the oxidation dye precursor to show various colors on hair, and examples thereof include, but are not limited to, 2-methyl-5-hydroxyethyl aminophenol, p-amino-o-cresol, m-aminophenol, 2,4-diaminophenoxyethanol hydrochloride, m-phenylenediamine hydrochloride, m-phenylenediamine, α-naphthol, resorcinol, and 2-methylresorcinol.

The first agent in the hair dye composition of the present invention may be used at a pH of 6-12 in the neutral to alkaline pH range. Preferably, it is used at an alkaline pH of 8-11. If the pH is lower than 6, the decomposition of the oxidizing agent contained in the second agent will not be easy, and the effect of increasing the hair cuticle and effectively penetrating the treatment agent into hair will be insignificant, and if the pH is higher than 12, damage to hair protein and skin irritation can occur.

The alkaline agent that is used in the present invention may be selected from among ammonia, monoethanolamine, aminomethylpropanol, isopropanolamine, sodium hydroxide, potassium hydroxide and the like, which are generally used in hair dyes.

In addition, the first agent in the hair dye composition of the present invention contains a water-soluble antioxidant and a reducing agent. Examples of water-soluble antioxidants that may be used in the present invention include ascorbic acid, erythorbic acid, and their salts, and examples of reducing agents that may be used in the present invention include sodium sulfite, sodium pyrosulfite, thioglycolic acid, thiolactic acid, cysteine, and their salts.

In addition, the first agent in the hair dye composition of the present invention may further contain a conventional direct dye within a range that does not impair the purpose of the present invention. Examples of this direct dye include Arianol dyes, p-nitro-o-phenylenediamine, nitro-p-phenylenediamine, 2-amino-4-nitrophenol, 2-amino-5-nitrophenol, nitro-p-phenylenediamine hydrochloride, picramic acid, and other vegetable dyes such as Henna.

In addition, the first agent in the hair dye composition of the present invention may further contain a conventional natural dye within a range that does not impair the purpose of the present invention, and examples of this natural dye include, but are not limited to, gallic acid, gallic acid esters, tannic acid and its ester, pyrogallol, logwood, Phellodendri cortex, Coptis chinensis, sappan wood, Lithospermum erythrorhizon, cochineal, indigo, madder, safflower, *Curcuma longa*, *Gardenia jasminoides*, *Sophora Japonica*, persimmon, *Galla rhois*, and *Alnus japonica*.

The second agent in the hair dye composition of the present invention contains an oxidizing agent. The oxidizing agent that is used in the present invention may be one or more selected from among hydrogen peroxide, urea iodine peroxide, alkali metal bromate, ferricyanide, perborate and persulfate, which are generally used in the art. Preferably, the oxidizing agent is hydrogen peroxide.

In addition, the second agent in the hair dye composition of the present invention may contain components, which are generally used in the art, within a range that does not impair the effect of the present invention. Examples of such components include emulsifiers such as paraffin, light liquid isoparaffin, higher fatty alcohols and higher fatty acid esters, cationic or non-ionic surfactants, stabilizers such as phenacetin, metal ion sequestering agents such as disodium EDTA, pH adjusters such as phosphoric acid, etc.

The first agent or second agent in the hair dye composition of the present invention may contain, in addition to the above-described components, conventional components that do not impair the effect of the present invention. Examples of such conventional components include, but are not limited, antioxidants, metal ion sequestering agents, solvents, surfactants, thickeners, fragrances, and conditioning agents.

Examples of the antioxidant include butylhydroxyanisole, dibutylhydroxytoluene, tert-butylhydroquinone, tocopherols, etc., and examples of the metal ion sequestering agent include EDTA, disodium EDTA, tetrasodium EDTA, pentasodium EDTA, etc. Examples of the solvent include ethanol, propyl alcohol, isopropyl alcohol, propylene glycol, hexylene glycol, diethylene glycol, etc. Examples of the surfactant include cationic surfactants, anionic surfactants, amphoteric surfactants, and nonionic surfactants, and examples of the thickener include polymeric thickeners, $C_{12}$-$C_{22}$ higher alcohols, and mixtures thereof, non-ionic polymers, anionic polymers, paraffin, light liquid isoparaffin, etc., and examples of the conditioning agent include a cationic polymer, a quaternary ammonium salt, silicone, etc.

Further, the first agent or second agent in the hair dye composition of the present invention contains, in addition to the above-described components, conventional water. Water that is used in the present invention is preferably purified water such as ion-exchanged water or distilled water. The content of water in the composition is not specifically limited and may be an amount capable of sufficiently dissolving or dispersing the components that are used in the hair dye composition.

In addition, the first agent or second agent in the hair dye composition of the present invention may contain a buffer which has a low molecular weight so as to be able to more effectively act on hair, and preferred examples of the buffer include organic acids, alkaline materials, and their salts. Specific examples of the buffer include potassium hydroxide, sodium hydroxide, ammonia water, phosphoric acid, glycolic acid, citric acid, acetic acid, hydrochloric acid, sulfuric acid, sodium carbonate and sodium salicylate/salicylic acid, and sodium carbonate and lactic acid/sodium lactate.

Also, the buffer is contained in an amount of 0.01-10 wt %, and preferably 0.1-5 wt %, based on the total weight of the hair dye composition. If the content of the buffer in the composition is less than 0.01 wt %, the effect of the buffer will be insufficient, and if the content of the buffer is more than 10 wt %, there can be a problem in terms of the stability of an easy-to use formulation.

Further, the foam-type hair dye composition of the present invention may contain, in addition to the first agent and the second agent, a third agent comprising an additive mixture.

The third agent comprising the additive mixture is composed of water, a solvent, an amphoteric surfactant and a cationic polymer at the following ratio. The content of the cationic polymer should be at least two times higher than the content of the amphoteric surfactant, and the total weight of the cationic polymer and the amphoteric surfactant should be 40-70 wt % based on the total weight of the third agent comprising the additive mixture. If the total weight of the cationic polymer and the amphoteric surfactant is less than 40 wt % based on the total weight of the third agent comprising the additive mixture, the effect of the present invention will be insignificant, and if it is more than 70 wt %, the miscibility of the third agent with the dye of the liquid first agent and the oxidizing agent of the second agent will be undesirably greatly reduced.

In addition, the total weight of water and the solvent in the third agent should be 30 wt % or more based on the total weight of the third agent in view of miscibility with the first and second agents, and if it is 60 wt % or more, the effect of the present invention will be insignificant. For this reason, the total weight of water and the solvent in the third agent should be less than 60 wt % based on the total weight of the third agent.

The amphoteric surfactant that is used in the third agent of the hair dye composition of the present invention may be selected from among various surfactants such as amine oxide type, betaine type, amino acid type and imidazoline type surfactants. Preferably, amine oxide type and amino acid type surfactants may be used alone or in a combination of two or more in the present invention.

In addition, the cationic polymer that is used in the third agent of the hair dye composition of the present invention may be a polymer containing an amino or ammonium group, a salt thereof or a polymer or copolymer of a salt thereof, but is not limited thereto.

When the third agent comprising the additive mixture is not separately provided and the components that are contained in the third agent are added to the dye of the first agent and the oxidizing agent of the second agent, the effect of the present invention will be reduced compared to the effect obtained when the third agent is separately provided. This is believed to be because of the influence of pH, and the pH of the third agent is not specifically limited, but the third agent is preferably used at a pH of 5-7.

The two-agent type or three-agent type foam-type hair dye composition according to the present invention can be provided in the form of an aerosol or non-aerosol, but is not limited thereto.

Immediately before application to hair, the two-agent type foam-type hair dye composition is used after mixing the first agent with the second agent, and the three-agent type foam-type hair dye composition is used after mixing the first agent with the second agent and the third agent. The mixture is placed in a foam container, and foam is discharged from the container and applied to hair. Herein, the mixing ratio of the agents is not specifically limited and is determined in view of dyeing ability and sensory feel. Particularly, in the case of the two-agent type composition according to the present invention, the first agent and the second agent are mixed at a ratio of 1:2, and in the case of the third-agent type composition, the first agent, the second agent and the third agent are mixed at a ratio of 3:6:1.

MODE FOR INVENTION

Hereinafter, the present invention will be described in detail with reference to examples and test examples. It is to be understood, however, that the present invention is not limited to these examples and test examples and can be embodied in various forms.

REFERENCE EXAMPLE 1

Preparation of Compositions of Examples and Comparative Examples

According to the compositions (unit: wt %) shown in Tables 1 to 3 below, a first agent, second agent and third agent for a hair dye composition were prepared by a conventional method. As a nonionic thickener, polyethylene glycol distearate containing 150 moles of ethylene oxide (that is, a compound of formula 5 wherein n is 150) was used. However, in addition to polyethylene glycol distearate, PEG-fatty acid diester, PPG-fatty acid diester, PEG-fatty acid monoester, PPG-fatty acid monoester, or other compounds containing 100-150 moles of ethylene oxide may all be used, and the effects of the use thereof are similar to the effect of the use of polyethylene glycol distearate (n=150).

TABLE 1

| First agent containing dye | |
| --- | --- |
| Components | Preparation Example 1 |
| EDTA-2Na | 0.2 |
| Erythorbic acid | 0.2 |
| Anhydrous sodium sulfite | 0.2 |
| Monoethanolamine | 8 |
| P-aminophenol | 0.2 |
| Toluene 2,5-diamine sulfate | 1 |
| P-amino-o-cresol | 0.8 |
| Butylene glycol | 5 |
| Propylene glycol | 5 |
| Purified water | To 100 |

TABLE 2

| | Second agent containing oxidizing agent | | | | | |
| --- | --- | --- | --- | --- | --- | --- |
| Components | Prep. Example 2 | Prep. Example 3 | Prep. Example 4 | Prep. Example 5 | Prep. Example 6 | Prep. Example 7 |
| Amidopropyl betaine | 10 | 10 | 10 | 10 | 10 | 10 |
| 1-hydroxyethane-1,1-diphosphonic acid liquid | 0.3 | 0.3 | 0.3 | 0.3 | 0.3 | 0.3 |
| Soyamidopropylamine oxide | 20 | 20 | 5 | 5 | 5 | — |
| Poly N,N'-dimethyl-3,5-dimethylene piperidinium chloride liquid | 5 | 5 | — | — | — | — |
| Stearyl alcohol | 1 | — | — | — | — | — |
| Polyethylene glycol distearate | — | — | — | 0.5 | 2 | 2 |
| Dipropylene glycol | 2 | 2 | 2 | 2 | 2 | 2 |
| Phosphoric acid | 0.3 | 0.3 | 0.3 | 0.3 | 0.3 | 0.3 |
| Hydrogen peroxide | 16.85 | 16.85 | 16.85 | 16.85 | 16.85 | 16.85 |
| Purified water | To 100 | To 100 | To 100 | To 100 | To 100 | To 100 |

TABLE 3

Third agent comprising additive mixture

| Components | Prep. Example 8 | Prep. Example 9 | Prep. Example 10 | Prep. Example 11 |
|---|---|---|---|---|
| Butylene glycol | 8 | 8 | 8 | 8 |
| Propylene glycol | 8 | 8 | 8 | 8 |
| Soyamidopropylamine oxide | 10 | 40 | — | 70 |
| Poly N,N'-dimethyl-3,5-dimethylene piperidinium chloride liquid | 15 | 15 | 35 | — |
| Polyquaternium-22 | 15 | 15 | 35 | — |
| Purified water | To 100 | To 100 | To 100 | To 100 |

The first agent, the second agent and the third agent were combined with each other as shown in Table 4 below to prepare compositions of Examples 1 to 7 and Comparative Examples 1 to 3. Herein, the compositions of Examples 1 to 3 and Comparative Examples 1 to 3 were prepared by mixing the first agent and the second agent at a ratio of 1:2, and the compositions of Examples 4 to 7 were prepared by mixing the first agent, the second agent and the third agent at a ratio of 3:6:1. These compositions of Examples 1 to 7 and Comparative Examples 1 to 3 were non-aerosol type compositions prepared by placing each of the contents of the first agent and the second agent or the first agent, the second agent and the third agent in a pumping container and sufficiently mixing the placed contents so that foam is discharged by pumping upon use.

TABLE 4

| | First agent | Second agent | Third agent |
|---|---|---|---|
| Comp. Example 1 | Prep. Example 1 | Prep. Example 2 | — |
| Comp. Example 2 | | Prep. Example 3 | — |
| Comp. Example 3 | | Prep. Example 4 | — |
| Example 1 | | Prep. Example 5 | — |
| Example 2 | | Prep. Example 6 | — |
| Example 3 | | Prep. Example 7 | — |
| Example 4 | | Prep. Example 6 | Prep. Example 8 |
| Example 5 | | Prep. Example 6 | Prep. Example 9 |
| Example 6 | | Prep. Example 6 | Prep. Example 10 |
| Example 7 | | Prep. Example 6 | Prep. Example 11 |

TEST EXAMPLE 1

Evaluation of Dyeing Ability

Each of the compositions of Examples 1 to 7 and Comparative Examples 1 to 3 was placed in a pumping container and mixed, and foam was discharged from the container. The amount of foam used was determined according to the weight of hair. The discharged foam was applied uniformly to virgin hair (black hair) and allowed to stand for 30 minutes. After the completion of application and maintenance, the hair was washed with running water for 1 minute using a shampoo liquid, and then dried with a hair dryer. The color of the dried hair was measured using a colorimeter (Hunterlab Labscan XE).

The results were expressed as $L^*$ values measured with the colorimeter before and after dyeing and were compared between the compositions. The $L^*$ value indicates whiteness, and a smaller $L^*$ value indicates a darker color, and thus better color rendition. The results are shown in Table 5 below.

TABLE 5

| Dyeing ability | Example 1 | Example 2 | Example 3 | Example 4 | Example 5 |
|---|---|---|---|---|---|
| $L^*$ | 23.11 | 23.21 | 22.89 | 20.02 | 22.34 |
| Dyeing ability | Example 6 | Example 7 | Comp. Example 1 | Comp. Example 2 | Comp. Example 3 |
| $L^*$ | 23.65 | 23.89 | 26.54 | 26.48 | 25.11 |

As can be seen in Table 5 above, the $L^*$ values of Examples 1 to 7 were smaller than the $L^*$ values of Comparative Examples to 3, suggesting that the compositions of Examples 1 to 7 have better color rendition than those of Comparative Examples 1 to 3.

In addition, it can be seen that the three-agent type compositions of Examples 4 and 5, which contain both the cationic polymer and the amphoteric surfactant, had better color rendition. Particularly, the composition of Example 4, which contains the cationic polymer in an amount that is more than two times larger than the amphoteric surfactant, showed the best color rendition. In addition, when only any one of the cationic polymer and the amphoteric surfactant was used, the dyeing ability decreased rather than increased.

TEST EXAMPLE 2

Evaluation of Color Persistence

The hair dyed with each of the compositions of Examples 1 to 7 and Comparative Examples 1 to 3 in Test Example 1 was added to a shampoo liquid and shaken using a shaker at a speed of 200 rpm for 30 minutes, after which the hair was rinsed with running water for 1 minute and dried with a hair dryer. This procedure was repeated three times, and then the difference in $L^*$ value between the compositions was analyzed using the colorimeter as described in Test Example 1, and the color persistence for each composition was evaluated based on the $\Delta L^*$ value. A smaller $\Delta L^*$ value indicates better color persistence. The results are shown in Table 6 below.

TABLE 6

| Persistence | Example 1 | Example 2 | Example 3 | Example 4 | Example 5 |
|---|---|---|---|---|---|
| $\Delta L^*$ | 2.88 | 2.91 | 2.52 | 1.55 | 2.78 |
| Persistence | Example 6 | Example 7 | Comp. Example 1 | Comp. Example 2 | Comp. Example 3 |
| $\Delta L^*$ | 3.52 | 3.03 | 4.92 | 4.84 | 4.55 |

As can be seen in Table 6 above, the $\Delta L^*$ values of the compositions of Examples 1 to 7 were significantly smaller than the $\Delta L^*$ values of the compositions of Comparative Examples 1 to 3, suggesting that the compositions of Examples 1 to 7 show color persistence much better than the compositions of Comparative Examples 1 to 3.

In addition, it can be seen that color persistence is the best in the three-agent type composition of Example 4, which contains both the cationic polymer and the amphoteric surfactant and in which the content of the cationic polymer is more than two times higher than that of the amphoteric surfactant.

TEST EXAMPLE 3

Evaluation of Damage to Hair

The evaluation of damage to hair was performed by evaluating both the conditioning of wet hair before shampooing and the conditioning of dry hair after drying. To evaluate damage to the hair dyed with each of the compositions of Examples 1 to 7 and Comparative Examples 1 to 3, the dyed hair was evaluated by 10 professional panels according to the following criteria, and the results of the evaluation are shown in Tables 7 and 8 below.

Criteria for Evaluation

⊚: very soft; ○: soft; Δ: somewhat coarse; X: coarse.

TABLE 7

|  | Example 1 | Example 2 | Example 3 | Example 4 | Example 5 |
|---|---|---|---|---|---|
| Damage to hair during rinsing | ○ | ○ | ○ | ⊚ | ⊚ |

|  | Example 6 | Example 7 | Comp. Example 1 | Comp. Example 2 | Comp. Example 3 |
|---|---|---|---|---|---|
| Damage to hair during rinsing | ○ | ○ | ⊚ | ⊚ | Δ |

TABLE 8

|  | Example 1 | Example 2 | Example 3 | Example 4 | Example 5 |
|---|---|---|---|---|---|
| Damage to dry hair | ○ | ○ | ○ | ⊚ | ○ |

|  | Example 6 | Example 7 | Comp. Example 1 | Comp. Example 2 | Comp. Example 3 |
|---|---|---|---|---|---|
| Damage to dry hair | ○ | ○ | Δ | Δ | X |

As can be seen in Table 7 above, damage to hair during rinsing appears to be less for the compositions of Comparative Examples 1 and 2 (containing an excessive amount of the amine oxide type surfactant) than for the compositions of Examples 1 to 3. However, as can be seen in Table 8 above, the softness of dry hair was significantly lower for the compositions of Comparative Examples 1 to 3, suggesting that the compositions of Comparative Examples 1 to 3 cause greater damage to hair. On the other hand, in the case of Examples 1 to 7, the softness of hair was maintained during rinsing and drying, and particularly, in the case of Example 4, there was little or no damage to hair, suggesting that the ability to maintain the softness of hair is very excellent.

TEST EXAMPLE 4

Evaluation of the Abilities to be Washed and Rinsed

The degree of washing of each of the hair dye compositions was evaluated based on the degree of slipperiness of the dyed hair when washing the dyed hair using a shampoo liquid in running water. The dyed hair was evaluated by 10 professional panels according to the following criteria, and the results of the evaluation are shown in Table 9.

Criteria for Evaluation

⊚: excellent; ○: good; Δ: somewhat weak; X: weak.

TABLE 9

|  | Example 1 | Example 2 | Example 3 | Example 4 | Example 5 |
|---|---|---|---|---|---|
| Abilities to be washed and rinsed | ⊚ | ⊚ | ⊚ | ⊚ | ⊚ |

TABLE 9-continued

|  | Example 6 | Example 7 | Comp. Example 1 | Comp. Example 2 | Comp. Example 3 |
|---|---|---|---|---|---|
| Abilities to be washed and rinsed | ⊚ | ⊚ | X | X | ⊚ |

As can be seen in Table 9 above, the compositions of Examples 1 to 7 have a very excellent ability to be washed, but in the case in the compositions of Comparative Examples 1 and 2 which contain a large amount of the amine oxide type surfactant, the dyeing ability is significantly reduced, and the ability to be washed is greatly reduced because the slippery feeling is maintained for a longer time than required.

TEST EXAMPLE 5

Evaluation of Skin Contamination

Whether the color applied to the skin during the evaluation of the dyeing ability is easily removed was evaluated by 10 professional panels according to the following criteria, and the results of the evaluation are shown in Table 10 below.

Criteria for Evaluation

⊚: very easily removed; ○: easily removed; Δ: not easily removed; X: not removed.

TABLE 10

|  | Example 1 | Example 2 | Example 3 | Example 4 | Example 5 |
|---|---|---|---|---|---|
| Removal of color from skin | ⊚ | ⊚ | ⊚ | ⊚ | ⊚ |

|  | Example 6 | Example 7 | Comp. Example 1 | Comp. Example 2 | Comp. Example 3 |
|---|---|---|---|---|---|
| Removal of color from skin | ⊚ | ⊚ | ○ | ○ | ○ |

As can be seen in Table 10 above, removal of the color applied to the skin was easier in the case of Examples 1 to 7 than in the case of Comparative Examples 1 to 3.

TEST EXAMPLE 6

Evaluation of Flowing Down of Content

The degree of the flowing down of the hair dye composition during application was evaluated by 10 professional panels according to the following criteria, and the results of the evaluation are shown in Table 11 below.

Criteria for Evaluation

⊚: not flowing down; Δ: slightly flowing down; X: excessively flowing down.

TABLE 11

|  | Example 1 | Example 2 | Example 3 | Example 4 | Example 5 |
|---|---|---|---|---|---|
| Flowing down | ◎ | ◎ | ◎ | ◎ | ◎ |

|  | Example 6 | Example 7 | Comp. Example 1 | Comp. Example 2 | Comp. Example 3 |
|---|---|---|---|---|---|
| Flowing down | ◎ | ◎ | Δ | Δ | X |

As can be seen in Table 11 above, in the case of Comparative Examples 1 to 3, the dye did flow down, but in the case of Examples 1 to 7, the dye did not flow down, suggesting that the compositions of Examples 1 to 7 are convenient to use.

The invention claimed is:

1. A hair dye composition comprising a first agent containing a dye and an alkaline agent, a second agent containing an oxidizing agent, and a third agent,
  wherein at least one of the first agent and the second agent comprises at least one nonionic thickener selected from the group consisting of polyethylene glycol-fatty acid diester, polypropylene glycol-fatty acid diester, polyethylene glycol-fatty acid monoester, and polypropylene glycol-fatty acid monoester;
  wherein the third agent is composed of water, a solvent, an amphoteric surfactant and a cationic polymer; and
  wherein the content of the cationic polymer is two times higher or more than the content of the amphoteric surfactant.

2. The hair dye composition of claim 1, wherein the composition is a foam-type composition.

3. The hair dye composition of claim 1, wherein the nonionic thickener is contained in the first agent or the second agent.

4. The hair dye composition of claim 1, wherein the nonionic thickener is contained in an amount of 0.1-5 wt % based on the total weight of the first agent and the second agent.

5. The hair dye composition of claim 1, wherein a sum content of the cationic polymer and the amphoteric surfactant is 40 wt % to 70 wt % based on the total weight of the third agent.

6. The hair dye composition of claim 1, wherein a content of the cationic polymer is 30 wt % and the content of the amphoteric surfactant is 15 wt %, based on the total weight of the third agent.

7. The hair dye composition of claim 1, wherein the amphoteric surfactant is an amine oxide-type or amino acid-type surfactant.

8. The hair dye composition of claim 1, wherein the cationic polymer is a polymer containing an amino group or an ammonium group.

9. The hair dye composition of claim 1, wherein the polyethylene glycol-fatty acid diester is polyethylene glycol distearate.

10. The hair dye composition of claim 1, wherein the cationic polymer is poly N,N'-dimethyl-3,5-dimethylene piperidinium chloride liquid or polyquaternium-22.

11. The hair dye composition of claim 1, wherein the amphoteric surfactant is isoamidoproylamine oxide.

* * * * *